US006869426B2

United States Patent
Ganem

(10) Patent No.: US 6,869,426 B2
(45) Date of Patent: Mar. 22, 2005

(54) ANTI-DRAWBACK MEDICAL VALVE

(75) Inventor: Charles F. Ganem, Cape Neddick, ME (US)

(73) Assignee: Nypro Inc., Clinton, MA (US)

(*) Notice: Subject to any disclaimer, the term of this patent is extended or adjusted under 35 U.S.C. 154(b) by 172 days.

(21) Appl. No.: 10/291,448

(22) Filed: Nov. 7, 2002

(65) Prior Publication Data

US 2003/0093061 A1 May 15, 2003

Related U.S. Application Data

(60) Provisional application No. 60/350,738, filed on Nov. 13, 2001.

(51) Int. Cl.[7] ........................ A61M 25/16; A61M 25/18; A61M 39/00; A61M 39/10
(52) U.S. Cl. ........................ 604/533; 604/246; 604/905; 251/149.1
(58) Field of Search ........................ 604/533, 246–256, 604/167.01–167.05, 200–202, 905; 251/149.1

(56) References Cited

U.S. PATENT DOCUMENTS

| | | | |
|---|---|---|---|
| 2,594,405 A | 4/1952 | Deters | 137/53 |
| 2,693,801 A | 11/1954 | Foreman | 128/214 |
| 2,705,501 A | 4/1955 | Frizsch et al. | 137/113 |
| 2,756,740 A | 7/1956 | Deane | 128/1 |
| 2,899,975 A | 8/1959 | Fernandez | 137/543.17 |
| 2,999,499 A | 9/1961 | Willett | 128/214 |
| 3,087,492 A | 4/1963 | Garth | 128/350 |
| 3,105,511 A | 10/1963 | Murphy, Jr. | 137/399 |
| 3,192,949 A | 7/1965 | De See | 137/540 |
| 3,385,301 A | 5/1968 | Harautuneian | 128/349 |
| 3,399,677 A | 9/1968 | Gould et al. | 128/349 |
| 3,416,567 A | 12/1968 | Von Dardel et al. | 137/604 |
| 3,506,005 A | 4/1970 | Gilio et al. | 128/214 |
| 3,538,950 A | 11/1970 | Porteners | 137/608 |
| 3,570,484 A | 3/1971 | Steer | 128/214 |
| 3,572,375 A | 3/1971 | Rosenberg | 137/512 |
| 3,726,282 A | 4/1973 | Patel | 128/349 BV |
| 3,806,086 A | 4/1974 | Cloyd | 251/149.7 |

(List continued on next page.)

FOREIGN PATENT DOCUMENTS

| | | |
|---|---|---|
| EP | 0268480 A1 | 5/1988 |
| EP | 0629418 A1 | 12/1994 |
| GB | 2 079 162 | 1/1982 |
| GB | 01/20218 A1 | 3/2001 |
| WO | 83/02559 | 8/1983 |
| WO | 93/11828 | 6/1993 |
| WO | 96/00107 | 1/1996 |
| WO | 97/39791 | 10/1997 |
| WO | 98/22178 | 5/1998 |
| WO | 98/26835 | 6/1998 |
| WO | 98/39594 | 9/1998 |
| WO | 00/44433 | 8/2000 |

*Primary Examiner*—Nicholas D. Lucchesi
*Assistant Examiner*—Catherine S. Williams
(74) *Attorney, Agent, or Firm*—Bromberg & Sunstein LLP

(57) ABSTRACT

A medical valve has an open mode that permits fluid flow, and a closed mode that prevents fluid flow. Among other things, the medical valve includes a housing forming an interior having a fluid chamber, and a valve mechanism within the interior. The valve mechanism has a movable member that includes a needle (e.g., a hypetube). The needle may extend into the fluid chamber when the valve is in the open mode.

16 Claims, 2 Drawing Sheets

U.S. PATENT DOCUMENTS

| | | |
|---|---|---|
| 3,831,629 A | 8/1974 | Mackal et al. ............... 137/525 |
| 3,923,065 A | 12/1975 | Nozick et al. ............... 128/348 |
| 3,965,910 A | 6/1976 | Fischer .................... 128/349 R |
| 3,994,293 A | 11/1976 | Ferro ...................... 128/214 R |
| 4,063,555 A | 12/1977 | Ulinder ................... 128/214 R |
| 4,094,195 A | 6/1978 | Friswell et al. ......... 73/422 GC |
| 4,094,196 A | 6/1978 | Friswell ................. 73/422 GC |
| 4,116,201 A | 9/1978 | Shah ........................ 128/351 |
| 4,121,585 A | 10/1978 | Becker, Jr. ............... 128/214 R |
| 4,143,853 A | 3/1979 | Abramson ............... 251/149.1 |
| 4,223,808 A | 9/1980 | Williams et al. ............... 222/88 |
| 4,300,571 A | 11/1981 | Waldbillig .................. 128/673 |
| 4,324,239 A | 4/1982 | Gordon et al. .......... 128/214 R |
| 4,333,455 A | 6/1982 | Bodicky .................. 128/214.4 |
| 4,334,551 A | 6/1982 | Pfister ................... 137/614.03 |
| 4,344,435 A | 8/1982 | Aubin .................... 128/350 R |
| 4,401,432 A | 8/1983 | Schwartz ..................... 604/89 |
| 4,421,296 A | 12/1983 | Stephens ................. 251/149.7 |
| 4,458,480 A | 7/1984 | Irwin ........................ 60/39.63 |
| 4,496,348 A | 1/1985 | Genese et al. .............. 604/167 |
| 4,498,658 A | 2/1985 | Mikiya .................... 251/149.6 |
| 4,534,758 A | 8/1985 | Akers et al. .................. 604/85 |
| 4,535,824 A | 8/1985 | Raines ...................... 137/854 |
| 4,550,785 A | 11/1985 | Hibbard et al. ............. 173/134 |
| 4,551,136 A | 11/1985 | Mandl ........................ 604/141 |
| 4,585,435 A | 4/1986 | Vaillancourt ................. 604/27 |
| 4,596,557 A | 6/1986 | Pexa ........................... 604/86 |
| 4,611,973 A | 9/1986 | Birdwell ..................... 417/342 |
| 4,617,015 A | 10/1986 | Foltz ......................... 604/100 |
| 4,661,110 A | 4/1987 | Fortier et al. ................ 604/256 |
| 4,675,003 A | 6/1987 | Hooven ......................... 604/9 |
| 4,681,132 A | 7/1987 | Lardner ..................... 137/271 |
| 4,683,905 A | 8/1987 | Vigneau et al. ............. 137/329 |
| 4,683,916 A | 8/1987 | Raines ...................... 137/854 |
| 4,698,061 A | 10/1987 | Makaryk et al. ............ 604/408 |
| 4,710,168 A | 12/1987 | Schwab et al. ............... 604/99 |
| 4,712,583 A | 12/1987 | Pelmulder et al. .......... 137/852 |
| 4,743,235 A | 5/1988 | Waldbillig et al. .......... 604/250 |
| 4,745,950 A | 5/1988 | Mathieu ..................... 137/798 |
| 4,749,003 A | 6/1988 | Leason ...................... 137/854 |
| 4,752,287 A | 6/1988 | Kurtz et al. .................. 604/99 |
| 4,752,292 A | 6/1988 | Lopez et al. ................ 604/244 |
| 4,758,224 A | 7/1988 | Siposs ........................ 604/119 |
| 4,776,369 A | 10/1988 | Lardner et al. .......... 137/515.5 |
| 4,809,679 A | 3/1989 | Shimonaka et al. ............ 128/4 |
| 4,816,020 A | 3/1989 | Brownell ..................... 604/97 |
| 4,819,684 A | 4/1989 | Zaugg et al. ................ 137/112 |
| 4,850,978 A | 7/1989 | Dudar et al. ................ 604/201 |
| 4,874,377 A | 10/1989 | Newgard et al. ............ 604/167 |
| 4,915,687 A | 4/1990 | Sivert .......................... 604/83 |
| 4,917,668 A | 4/1990 | Haindl ....................... 604/167 |
| 4,935,010 A | 6/1990 | Cox et al. ................... 604/122 |
| 4,966,199 A | 10/1990 | Ruschke ..................... 137/843 |
| 5,006,114 A | 4/1991 | Rogers et al. ............... 604/167 |
| 5,041,087 A | 8/1991 | Loo et al. ..................... 604/83 |
| 5,048,537 A | 9/1991 | Messinger .................. 128/673 |
| 5,049,128 A | 9/1991 | Duquette ..................... 604/83 |
| 5,059,175 A | 10/1991 | Hanover et al. .......... 604/891.1 |
| 5,080,654 A | 1/1992 | Picha et al. ................. 604/167 |
| 5,085,645 A | 2/1992 | Purdy et al. ................ 604/167 |
| 5,100,394 A | 3/1992 | Dudar et al. ................ 604/283 |
| 5,108,380 A | 4/1992 | Herlitze et al. ............. 604/283 |
| 5,147,333 A | 9/1992 | Raines ....................... 604/249 |
| 5,171,230 A | 12/1992 | Eland et al. ................. 604/250 |
| 5,199,947 A | 4/1993 | Lopez et al. .................. 604/56 |
| 5,201,715 A | 4/1993 | Masters ...................... 604/175 |
| 5,203,775 A | 4/1993 | Frank et al. ................ 604/256 |
| 5,215,538 A | 6/1993 | Larkin ........................ 604/249 |
| 5,221,271 A | 6/1993 | Nicholson et al. .......... 604/283 |
| 5,230,706 A | 7/1993 | Duquette ..................... 604/83 |
| 5,242,393 A | 9/1993 | Brimhall et al. .............. 604/86 |
| 5,242,432 A | 9/1993 | DeFrank .................... 604/284 |
| 5,269,771 A | 12/1993 | Thomas et al. ............. 604/213 |
| 5,280,876 A | 1/1994 | Atkins ..................... 251/149.1 |
| 5,300,034 A | 4/1994 | Behnke et al. .............. 604/167 |
| 5,320,328 A | 6/1994 | Decloux et al. ............. 251/326 |
| 5,330,435 A | 7/1994 | Vaillancourt ................ 604/167 |
| 5,349,984 A | 9/1994 | Weinheimer et al. .. 137/543.21 |
| 5,360,413 A | 11/1994 | Leason et al. ............... 604/249 |
| 5,380,306 A | 1/1995 | Brinon ....................... 604/244 |
| 5,390,898 A | 2/1995 | Smedley et al. .......... 251/149.6 |
| 5,401,255 A | 3/1995 | Sutherland et al. .......... 604/247 |
| 5,439,451 A | 8/1995 | Collinson et al. ............ 604/247 |
| 5,465,938 A | 11/1995 | Werge et al. ............. 251/149.1 |
| 5,474,536 A | 12/1995 | Bonaldo ...................... 604/86 |
| 5,474,544 A | 12/1995 | Lynn ......................... 604/283 |
| 5,487,728 A * | 1/1996 | Vaillancourt ................. 604/86 |
| 5,509,433 A | 4/1996 | Paradis ......................... 137/1 |
| 5,509,912 A | 4/1996 | Vaillancourt et al. ........ 604/283 |
| 5,514,116 A * | 5/1996 | Vaillancourt et al. ........ 604/537 |
| 5,520,666 A | 5/1996 | Choudhury et al. ........ 604/283 |
| 5,533,708 A | 7/1996 | Atkinson et al. ......... 251/149.1 |
| 5,533,983 A | 7/1996 | Haining ..................... 604/249 |
| 5,549,566 A | 8/1996 | Elias et al. .................. 604/167 |
| 5,569,209 A | 10/1996 | Roitman ..................... 604/190 |
| 5,569,235 A | 10/1996 | Ross et al. .................. 604/403 |
| 5,573,516 A | 11/1996 | Tyner ......................... 604/249 |
| 5,578,059 A | 11/1996 | Patzer ........................ 604/249 |
| 5,616,129 A | 4/1997 | Mayer ........................ 604/167 |
| 5,616,130 A | 4/1997 | Mayer ........................ 604/167 |
| 5,620,434 A | 4/1997 | Brony ........................ 604/406 |
| 5,674,206 A | 10/1997 | Allton et al. ................ 604/249 |
| 5,676,346 A | 10/1997 | Leinsing ................... 251/149.1 |
| 5,685,866 A | 11/1997 | Lopez ........................ 604/249 |
| 5,694,686 A | 12/1997 | Lopez ................... 29/890.126 |
| 5,695,466 A | 12/1997 | Lopez et al. ................... 604/93 |
| 5,699,821 A | 12/1997 | Paradis ........................... 137/1 |
| 5,700,248 A | 12/1997 | Lopez ........................ 604/249 |
| 5,749,861 A | 5/1998 | Guala et al. ................. 604/249 |
| RE35,841 E | 7/1998 | Frank et al. ................. 604/256 |
| 5,776,113 A * | 7/1998 | Daugherty et al. .......... 604/537 |
| 5,806,831 A | 9/1998 | Paradis .................... 251/149.1 |
| 5,820,601 A | 10/1998 | Mayer ........................ 604/167 |
| 5,921,264 A | 7/1999 | Paradis ........................ 137/15 |
| 6,029,946 A | 2/2000 | Doyle ...................... 251/149.1 |
| 6,036,171 A | 3/2000 | Weinheimer et al. ..... 251/149.1 |
| 6,039,302 A | 3/2000 | Cote, Sr. et al. .......... 251/149.1 |
| 6,048,335 A | 4/2000 | Mayer ........................ 604/167 |
| 6,050,978 A | 4/2000 | Orr et al. .................... 604/249 |
| 6,068,011 A | 5/2000 | Paradis ........................... 137/1 |
| 6,089,541 A | 7/2000 | Weinheimer et al. ..... 251/149.6 |
| 6,152,900 A | 11/2000 | Mayer ........................ 604/167 |
| 6,245,048 B1 | 6/2001 | Fangrow, Jr. et al. ........ 604/249 |
| 6,290,206 B1 | 9/2001 | Doyle ...................... 251/149.1 |
| 6,344,033 B1 | 2/2002 | Jepson et al. ................ 604/256 |
| 6,428,520 B1 | 8/2002 | Lopez et al. ................ 604/249 |
| 6,543,745 B1 | 4/2003 | Enerson ................... 251/149.7 |
| 6,595,964 B2 | 7/2003 | Finley et al. ................ 604/246 |
| 6,595,981 B2 * | 7/2003 | Huet .......................... 604/523 |
| 6,609,696 B2 | 8/2003 | Enerson ....................... 251/86 |
| 2003/0098430 A1 | 5/2003 | Leinsing et al. .......... 251/149.6 |
| 2003/0141477 A1 | 7/2003 | Miller ..................... 251/149.1 |

\* cited by examiner

ANTI-DRAWBACK MEDICAL VALVE

PRIORITY

This patent application claims priority from provisional U.S. patent application No. 60/350,738, filed Nov. 13, 2001, entitled, "ANTI-DRAWBACK MEDICAL VALVE," and naming Charles F. Ganem as inventor, the disclosure of which is incorporated herein, in its entirety, by reference.

CROSS REFERENCE TO RELATED APPLICATIONS

This application is related to the following U.S. provisional and non-provisional patent applications, the disclosures of which are incorporated herein, in their entireties, by reference:

- application Ser. No. 09/479,327 (Bromberg & Sunstein LLP);
- application Ser. No. 09/812,237 (Bromberg & Sunstein LLP);
- application Ser. No. 10/007,377 (Bromberg & Sunstein LLP);
- Application No. 60/350,775 (Bromberg & Sunstein LLP);
- application Ser. No. 10/224,299 (Bromberg & Sunstein LLP); and
- Application No. 60/422,074 (Bromberg & Sunstein LLP), entitled, "Positive Push Medical Valve with Internal Seal," filed Oct. 29, 2002, and naming Brian Newton and Andy Cote as joint inventors.

FIELD OF THE INVENTION

The invention generally relates to medical products and, more particularly, the invention relates to devices for reducing backflow through a medical valve.

BACKGROUND OF THE INVENTION

In general terms, medical valving devices often act as a sealed port that may be repeatedly accessed to non-invasively inject fluid into (or withdraw fluid from) a patient's vasculature. Consequently, a medical valve permits the patient's vasculature to be freely accessed without requiring such patient's skin be repeatedly pierced by a needle.

Medical personnel insert a syringe into the medical valve to inject fluid into (or withdraw fluid from) a patient who has an appropriately secured medical valve. Once inserted, fluid may be freely injected into or withdrawn from the patient. Problems arise, however, when the syringe is withdrawn from the valve. Specifically, a back pressure (i.e., a proximally directed pressure) produced by the withdrawing syringe undesirably can cause blood to be drawn proximally into the valve. In addition to coagulating and impeding the mechanical operation of the valve, blood in the valve also compromises the sterility of the valve.

SUMMARY OF THE INVENTION

In accordance with one aspect of the invention, a medical valve has an open mode that permits fluid flow, and a closed mode that prevents fluid flow. Among other things, the medical valve includes a housing forming an interior having a fluid chamber, and a valve mechanism within the interior. The valve mechanism has a movable member that includes a needle (e.g., a hypotube). The needle extends into the fluid chamber when the valve is in the open mode.

In illustrative embodiments, the movable member forms a fluid channel that is open when in the open mode, and closed when in the closed mode. In such embodiment, the needle has a generally distally located opening. The generally distally located opening is occluded by a membrane when in the closed mode.

BRIEF DESCRIPTION OF THE DRAWINGS

The foregoing and other advantages of the invention will be appreciated more fully from the following further description with reference to the accompanying drawings wherein.

DESCRIPTION OF ILLUSTRATIVE EMBODIMENTS

In illustrative embodiments, a medical valve is configured to reduce drawback to relatively negligible volumes. Details are discussed below.

Figure 1:
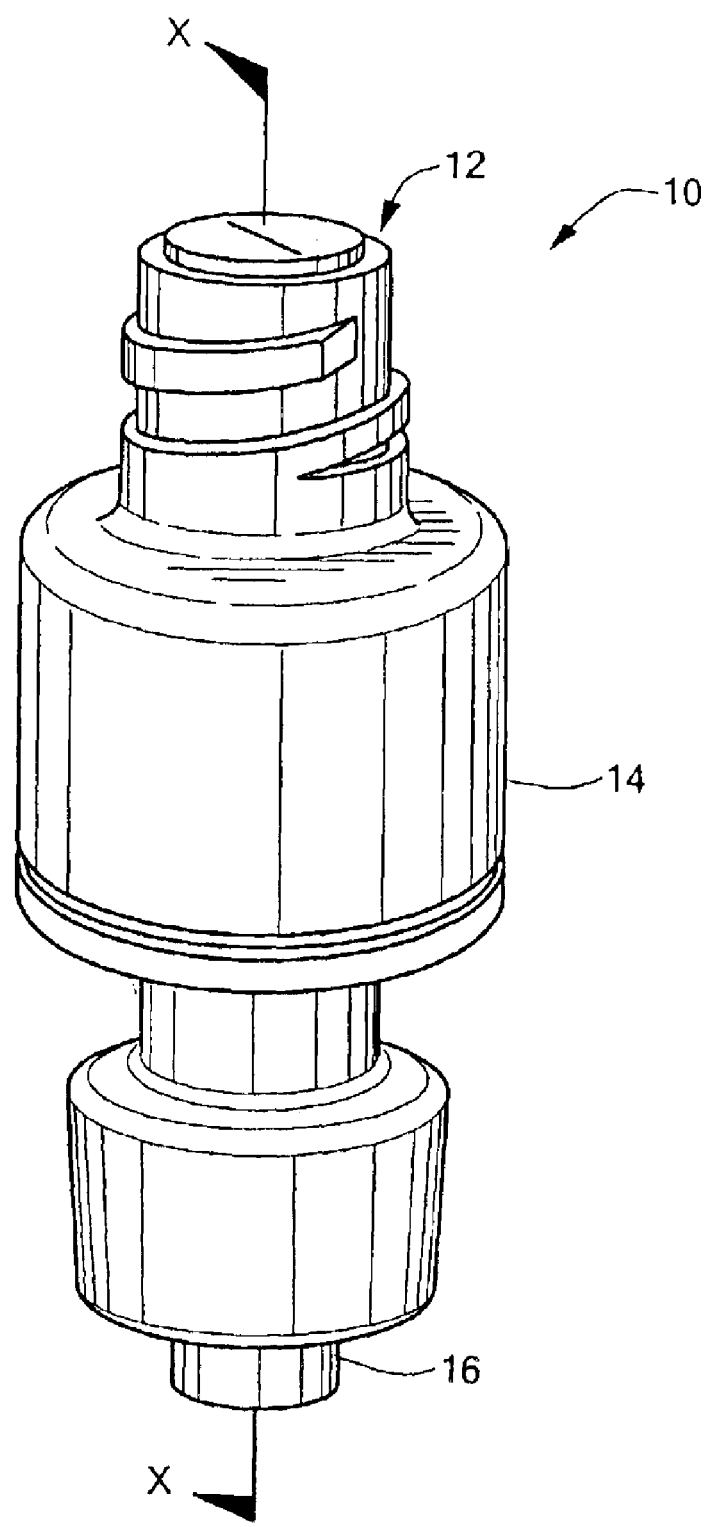
FIG. 1 schematically shows a medical valve configured in accordance with illustrative embodiments of the invention.

FIG. 1 schematically shows a medical valve 10 that is configured to reduce fluid drawback (a/k/a "back-flow") when a syringe or other type of nozzle is withdrawn from it. The valve 10 includes a proximal port 12 for receiving the nozzle, a valve body 14 having an internal valve mechanism (shown in FIG. 2) that controls fluid flow through the valve 10, and a distal port 16 for directing fluid between the valve 10 and a patient. The distal port 16 of the valve 10 may be at its location shown in FIG. 1, or at a location that is orthogonal to the longitudinal dimension of the valve 10. The fluid preferably is in liquid form, such as liquid medication. Although much of the discussion herein refers to the proximal port 12 as a fluid inlet, and the distal port 16 as a fluid outlet, the proximal and distal ports 12 and 16 also may be respectively utilized as outlet and inlet ports.

In illustrative embodiments, the valve 10 has components that are similar to the luer-activated swab valve disclosed in U.S. Pat. No. 6,039,302 entitled, "SWABBABLE LUER-ACTIVATED VALVE," the disclosure of which is incorporated herein, in its entirety, by reference. Of course, various embodiments may relate to other types of valves and thus, such embodiments are not limited to swab valves and/or luer-activated valves. Other embodiments are related to those shown in the above noted pending U.S. patent application Ser. Nos. 09/479,327 and 09/812,237.

Figure 2:
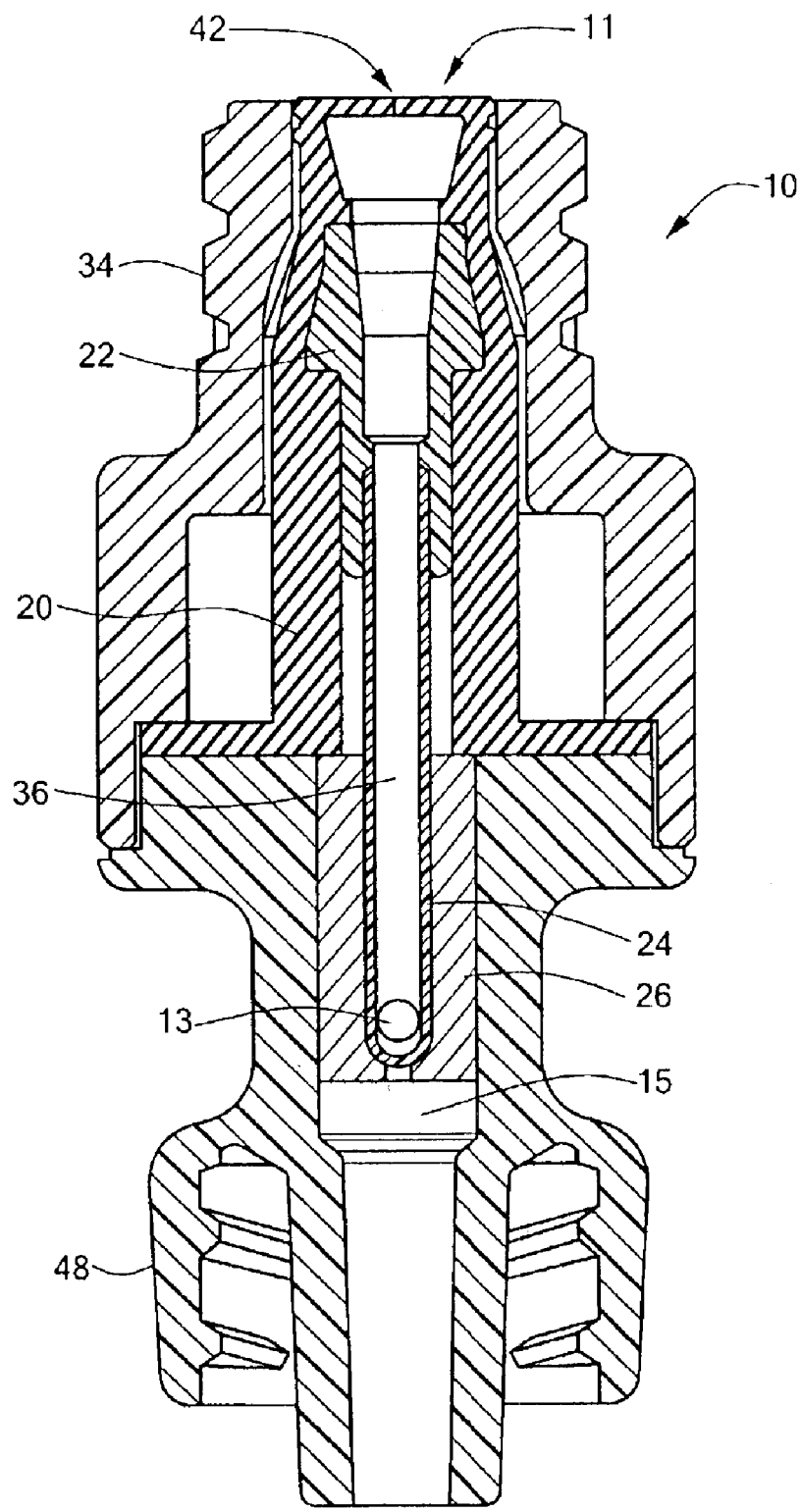
FIG. 2 schematically shows a cross-sectional view of the medical valve shown in FIG. 1.

FIG. 2 schematically shows one embodiment of the medical valve 10 (shown in FIG. 1 along line X—X) in a closed position. More particularly, FIG. 2 schematically shows a cross-sectional view of an embodiment of the medical valve 10 shown in FIG. 1, which is configured to reduce fluid drawback (a/k/a "back-flow") when a syringe or other type of nozzle is withdrawn from it.

Among other things, the valve 10 includes an inlet housing portion 34 that is coupled with an outlet housing portion 48 to form a valve interior. Any conventional coupling means may be used, such as ultrasonic welding or conventional snap-fit techniques. The valve interior includes a valve mechanism to control fluid flow through the valve 10. The valve mechanism includes a stretchable and compressible gland 20 secured between the inlet housing 34 and outlet housing 48, a rigid and longitudinally movable cannula 22 secured within the valve 10 by the gland 20, and a membrane 26 to partially occlude fluid flow from the cannula 22.

The cannula 22 includes a proximal section that is coupled with a distally located thin section. In illustrative embodiments, the thin section is a hollow needle (identified by reference number "24") that, together with the proximal section, form a flow channel 36. The needle 24 is open at its proximal end, closed at its distal end, and has a hole 13 in its side just proximal to its distal end. When in the closed position, the hole 13 is occluded by the membrane 26, which is held fixed between outlet housing 48 and the gland 20.

The outlet housing 48 forms a chamber 15 having a volume that changes slightly as the needle 24 is urged proximally and distally by a nozzle. In particular, the volume of the chamber 15 is slightly greater when in the closed mode than when in the open mode. This slight difference in volume is due to the volume of the needle extending into the chamber 15.

Insertion of a nozzle against a slit 42 at the proximal end of the gland 20 causes the cannula 22 to move distally, thereby moving the hole 13 from its occluding contact with the membrane 26. Liquid consequently may be directed first through the flow channel 36 and hole 13, then through the chamber 15, and out of the valve 10 through the distal port 16.

In an illustrative embodiment of the invention, the needle 24 is sized to be very thin. The amount of fluid drawn back into the chamber 15 as the nozzle is withdrawn corresponds to the volume of the needle 24 required to expose the hole 13 to the chamber 15. Consequently, as suggested above, this volume is controlled by the needle diameter and the placement of the hole 13. By making the diameter of the needle 24 small and the hole 13 very close to the distal end of the needle 24, the volume of fluid drawn back into the chamber 15 is reduced and the subsequent risk from contamination to the valve 10 minimized. In certain embodiments, the volume of fluid drawn back upon withdrawal of the nozzle is of the order of between about one and several microliters. In some embodiments, the total volume of fluid drawn back is on the order of about 0.5 microliters.

An exemplary embodiment of the invention may have a total length of about 1.160 centimeters, a maximum width of about 0.440 centimeters, and a priming volume of 0.033 cubic centimeters. The priming volume is measured as the interior volume distal of the needle 24 when in the closed position.

In some embodiments, a bump or other type of protrusion can be included on the needle 24 to pull (i.e., stretch) the membrane 26 back beyond its normally neutral position. In so doing, the membrane 26 is pulled to a point at which the membrane 26 will be released from the bump on the needle 24. As the membrane 26 returns to its neutral position, it pushes fluid forward through the outlet (referred to herein as "positive push"). In still other embodiments, the bump may be a part of the membrane 26.

It is contemplated that the amount of fluid pushed forward by this bump can be controlled to cancel out with the amount of drawback caused by the needle 24 returning into the membrane 26. In other words, the volume of the internal chamber 15 remains substantially constant as the valve transitions between the open and closed modes. When this occurs, a meniscus at the distal port 16 (when the distal port is facing upwardly, such as during priming) will be substantially unchanged as the nozzle is withdrawn from the valve 10. Accordingly, in this case, the valve 10 has neither a positive push nor a drawback when the it transitions from the open mode to the closed mode. In practice, this embodiment can have negligible amounts in either direction (e.g., less then one microliter). This design, which has insubstantial drawback and/or positive push, thus may be considered to have a "neutral" drawback.

In illustrative embodiments, the distal end of the needle is bulbous to facilitate its movement through the membrane 26. In such embodiment, the hole 13 is located immediately above the bulbous distal end. In other embodiments, the membrane 26 and gland 20 are a single unitary molded part.

Although an exemplary embodiment of the invention has been disclosed, it should be apparent to those skilled in the art that various changes and modifications can be made which will achieve some of the advantages of the invention without departing from the true scope of the invention.

I claim:

1. A medical valve having an open mode that permits fluid flow, and a closed mode that prevents fluid flow, the medical valve comprising:

a housing forming an interior having a fluid chamber;

a valve mechanism within the interior, the valve mechanism having a movable member, the movable member including a needle that extends into the fluid chamber when the valve is in the open mode, the entire needle moving as the valve transitions from the open mode to the closed mode, wherein the valve has neither a positive push nor a drawback when the valve transitions from the open mode to the closed mode.

2. The medical valve as defined by claim 1 wherein the movable member forms a fluid channel that is open when in the open mode, and closed when in the closed mode.

3. The medical valve as defined by claim 1 wherein the needle is a tube.

4. The medical valve as defined by claim 1 wherein the needle is at least a part of a cannula.

5. The medical valve as defined by claim 1 wherein the needle has a side wall that terminates at a closed distal end, the side wall forming a hole that is occluded by the valve mechanism when in the closed mode.

6. The medical valve as defined by claim 5 further including a member that occludes the hole when in the closed mode.

7. The medical valve as defined by claim 1 further wherein the valve mechanism includes a gland circumscribing at least a portion of the movable member.

8. The medical valve as defined by claim 1 wherein the housing forms a proximal port, the valve mechanism forming a seal at the proximal port when in the closed mode, the valve mechanism also forming a seal within the interior of the housing when in the closed mode.

9. The medical valve as defined by claim 1 wherein the needle is a hypotube.

10. The medical valve as defined by claim 1 wherein the entire needle moves longitudinally as the valve transitions from the open mode to the closed mode.

11. A medical valve having an open mode that permits fluid flow, and a closed mode that prevents fluid flow, the medical valve comprising:

a housing forming a proximal port and a distal port, the housing also having a fluid chamber positioned closer to the distal port than to the proximal port;

a valve mechanism between the proximal port and distal port, the valve mechanism having a movable member with a movable needle that extends into the fluid chamber when the valve is in the open mode, the needle having a side wall that terminates at a closed distal end, the side wall forming a hole that is normally occluded by the valve mechanism, the valve having neither a positive push nor a drawback when the valve transitions from the open mode to the closed mode.

12. The medical valve as defined by claim 11 further including a proximal seal adjacent the proximal port, the proximal seal being substantially flush with the proximal port.

13. The medical valve as defined by claim 11 wherein the needle is a tube.

14. The medical valve as defined by claim 11 wherein the valve mechanism includes a member that occludes the hole when in the closed mode.

15. The medical valve as defined by claim 11 further wherein the valve mechanism includes a gland circumscribing at least a portion of the movable member.

16. The medical valve as defined by claim 11 wherein the entire needle moves longitudinally as the valve transitions from the open mode to the closed mode.

* * * * *